United States Patent [19]

Hayman et al.

[11] Patent Number: 5,260,419
[45] Date of Patent: Nov. 9, 1993

[54] PURIFICATION OF ACTIVE AND INACTIVE/LATENT FORMS OF PLASMINOGEN ACTIVATOR INHIBITOR-1

[75] Inventors: Alan C. Hayman, The Woodlands, Tex.; Jodie L. Duke, Jr., Newark, Del.

[73] Assignee: The DuPont Merck Pharmaceutical Company, Wilmington, Del.

[21] Appl. No.: 671,433

[22] Filed: Mar. 20, 1991

[51] Int. Cl.$^5$ .................. C07K 3/02; C07K 3/22; C07K 15/06; C07K 15/14
[52] U.S. Cl. ..................... 530/380; 530/395; 530/416
[58] Field of Search ............... 530/350, 380, 395, 412, 530/416, 341 C

[56] References Cited

U.S. PATENT DOCUMENTS 5,073,626 12/1991 Wun .................... 530/413
5,134,065 7/1992 Sanzo et al. ............ 530/380

FOREIGN PATENT DOCUMENTS 260757 3/1988 European Pat. Off. .
88/01273 2/1988 PCT Int'l Appl. .

OTHER PUBLICATIONS

Reilly et al., J. Biol. Chem. 265:9570-9574 (1990).
Lawrence et al., Eur. J. Biochem. 186:523-533 (1989).
Franke et al., Biochim. Biophys. Acta 1037:16-23 (1990).
Lambers et al., Fibrinolysis 2, Supp. 1:33 (1988).
Lawrence et al., Fibrinolysis 2, Supp. 1:54 (1988).
Ny et al., Proc. natil. Acad. Sci. USA. 83:6776-6780 (1986).
Wun et al., FEBS Letters 210:11-16 (1987).
Alessi et al., Eur. J. Biochem. 175:531-540 (1988).
Pannekoek et al., EMBO J. 5:2539-2544 (1986).
Wun et al., J. Biol. Chem. 264:7862-7868 (1989).

Primary Examiner—Jeffrey E. Russel
Attorney, Agent, or Firm—Blair Q. Ferguson

[57] ABSTRACT

A method of separating active and inactive/latent forms of PAI-1 is disclosed comprising loading a sample containing a mixture of active and inactive/latent forms of PAI-1 to either an anion or cation exchange resin of 10-50 micron particle size and eluting active and inactive/latent forms of PAI-1 from the resin into separate fractions. Also disclosed is a method of extracting soluble E. coli-expressed recombinant PAI-1 from the lysed E. coli host cells in a buffered solution, wherein the ionic strength of the buffered solution is 8-25 millisiemens.

10 Claims, 2 Drawing Sheets

PURIFICATION OF ACTIVE AND INACTIVE/LATENT FORMS OF PLASMINOGEN ACTIVATOR INHIBITOR-1

BACKGROUND OF THE INVENTION

Human tissue-type plasminogen activator (t-PA) is a key physiological regulator of fibrinolysis. It converts the zymogen plasminogen into plasmin, the enzyme which degrades the fibrin network of the thrombus. Apparently, in the presence of a clot, both t-PA and plasminogen bind to fibrin and form a ternary complex in which plasminogen is efficiently activated. The affinity for fibrin makes t-PA clot-specific, and useful as a therapeutic agent for fibrinolytic therapy in man.

The principal physiological regulator of t-PA appears to be a specific, fast-acting, plasminogen activator inhibitor type-1 (PAI-1). PAI-1 is a protein of Mr 50,000 which binds to t-PA in a 1:1 complex, and inactivates the serine protease. Recent clinical studies suggest that elevated levels of PAI-1, by reducing the net endogenous fibrinolytic capacity, may contribute to the pathogenesis of various thrombotic disorders, including myocardial infarction, deep vein thrombosis, and disseminated intravascular coagulation.

The existence of two forms of PAI-1 differing in t-PA inhibitory activity and referred to as active and inactive or latent (inactive/latent), has been described previously. PAI-1 isolated from many mammalian cell types is obtained in a partially active latent form; the latent form is known to be converted to a more active form, by treatment with denaturants such as sodium dodecylsulfate (SDS). In addition, both active and inactive/latent forms of PAI-1 expressed in *E. coli* have been reported, as discussed below.

The expression in bacteria and purification of recombinant human PAI-1 cDNA has previously been reported. Ny et al. (1986) Proc. Natl. Acad. Sci. USA 83:6776-6780 disclosed the expression of functional rPAI-1 in *E. coli*, using a phage lambda gt11-derived vector. rPAI-1 was expressed as a beta-galactosidase-PAI-1 fusion protein of about 180 kDa, with the PAI-1 coding sequence fused to the *E. coli* beta-galactosidase coding sequence. Wun and Kretzmer (1987) FEBS Letters 210:11-16 similarly used a lambda gt11 expression vector to express functional rPAI-1 in *E. coli*. Pannekoek et al. (1986) EMBO J. 5:2539-2544 reported the expression of a functional 43 kDa form of rPAI-1 in *E. coli* using a pUC9-derived vector, as assayed by reverse fibrin autography. Although Ny et al., Pannekoek et al., and Wun and Kretzmer report the expression of functional rPAI-1 in *E. coli*, they did not report the purification of the *E. coli*-expressed rPAI-1 and did not quantitate the specific activity of the crude preparations of rPAI-1.

It has been reported from the Pannekoek group that rPAI-1 is expressed in *E. coli* almost exclusively in an inactive or latent form (Lambers et al. *Fibrinolysis* (1988) 2, Supp. 1:33). Apparently the 43 kDa form reported by Pannekoek et al. (1986) EMBO J. 5:2539-2544 is predominantly inactive. Another recent report states that rPAI-1 expressed in *E. coli* has biological activity toward urokinase almost equal to that of human fibrosarcoma PAI-1 (Lawrence et al. *Fibrinolysis* (1988) 2, Supp.1:54).

We previously reported the production of substantially pure, biologically functional, nonfused mature form *E. coli*-expressed human recombinant PAI-1 (rPAI-1) protein having a specific activity of about 300,000 units/mg, where a unit is defined as the amount of protein required to neutralize 1 international unit of t-PA in an S2288 chromogenic assay, where the enzymatic activity of t-PA to generate plasma from its plasminogen precursor is measured (Reilly et al., (1990) J. Biol. Chem. 265:9570-9574; copending, commonly assigned U.S. Ser. No. 07/350264, filed May 11, 1989). The biological activity of this preparation of PAI-1, was not significantly enhanced by treatment with protein denaturants.

We have previously reported the purification of rPAI-1 using a process including Q-Sepharose (anion exchanger) and S-Sepharose (cation exchanger) chromatography steps (Reilly et al., *J. Biol. Chem.* (1990) 265:9570-9574; U.S. Ser. No. 07/350,264, filed May 11, 1989). However, it was not suggested in these references that such ion exchange chromatography steps could be used to provide the resolution and separation of active form and inactive/latent form rPAI-1.

The separation of active and inactive/latent forms of PAI-1 using a single chromatographic step has not previously been disclosed. Indeed, the inability of previous researchers to resolve the active and inactive/latent forms of PAI-1 has presented a major difficulty in obtaining homogeneous active form PAI-1, or PAI-1 compositions of defined proportion of active form and inactive/latent forms. For example, Franke et al. *Biochim. Biophys. Acta* (1990) 1037:16-23) report that "Although isolation of active PAI-1 was of interest in principle, the pronounced lability of the inhibitory activity was considered to make this an unrealistic goal". Franke et al. consequently only reported a partly purified preparation of active form rPAI-1.

Lawrence et al. (*Eur. J. Biochem.* (1989) 186:523-533) reported the production and purification of rPAI-1. The purified *E. coli*-expressed rPAI-1 of Lawrence et al. was reported to have a specific activity similar to activated eukaryotic-expressed (natural or recombinant) PAI-1 and a percentage of the maximum theoretical inhibition of about 50%. Thus, the preparation *E. coli*-expressed rPAI-1 of Lawrence et al. appears to contain a mixture of active and inactive/latent forms. Significantly, Lawrence et al. do not report the resolution of active and inactive/latent form rPAI-1 using a chromatographic process. Lawrence et al. use the following chromatography steps: gel filtration (Sephacryl S-200), hydroxylapatite, and heparin-agarose. Indeed, Lawrence et al. report that the inactive/latent form and the activated form (guanidine-treated) of eukaryotic rPAI-1 have identical elution profiles on gel filtration chromatography.

SUMMARY OF THE INVENTION

We have discovered a method for separating active form PAI-1, having a specific activity of greater than about 500,000 units/mg in the S-2251 assay, and inactive/latent form of PAI-1, having a specific activity of less than about 5,000 units/mg in the S-2251 assay, comprising loading a sample containing both active and inactive/latent forms of PAI-1 to a cation exchange resin of 10-50 micron particle size and eluting active and inactive/latent forms of PAI-1 into separate fractions. The particle size of the cation exchange resin is preferably of relatively uniform particle size of 10-50 micron particle size. By "relatively uniform particle size" it is meant that the particle sizes of the resin are in the range of about plus or minus 10-20%. The sample loaded preferably contains at least 0.3 mg of total PAI-1 (both active and inactive/latent forms) per 1 mg of total protein.

The cation exchange resin may be loaded using a buffer of ionic strength of about 5-50 millisiemens as measured by conductivity and a pH of about 5.5-7. The buffer ionic strength of the sample loaded is preferably about 8-50 millisiemens.

Active and inactive/latent forms of PAI-1 are eluted into separate fractions from the cation exchange resin using a mobile phase buffer with a gradient of increasing ionic strength. Alternatively, active and inactive/latent forms of PAI-1 are eluted into separate fractions from the cation exchange resin using a mobile phase buffer with a gradient of increasing pH. Active and inactive/latent forms of PAI-1 are also eluted into separate fractions from the cation exchange resin using a mobile phase buffer with a gradient of both increasing ionic strength and pH.

Both recombinant and nonrecombinant PAI-1 are known to exist in forms that differ in tPA inhibitory activity. The tPA inhibitory activity of active form PAI-1 is much greater than the specific activity of inactive or latent forms of PAI-1. Both inactive and latent forms of PAI-1 have low specific tPA inhibitory activity of less than about 5,000 units/mg as determined in the S2288 chromogenic assay described in copending, commonly assigned U.S. patent application U.S. Ser. No. 07/350,264, filed May 11, 1989. Inactive and latent PAI-1 differ in that the tPA inhibitory activity of latent PAI-1 can be activated or stimulated, for example, by treatment with protein denaturants, whereas inactive PAI-1 cannot be activated in this manner.

The ion exchange chromatography methods of purifying PAI-1 described herein do not distinguish between or separate inactive and latent forms of PAI-1. Inactive and latent forms of PAI-1 are referred to herein collectively as inactive/latent form of PAI-1.

Active and inactive or latent (inactive/latent) forms of PAI-1 can be separated and purified by elution into separate fractions from a cation exchange resin of particle (or bead) size of about 10-50 microns, where the resin is loaded using a buffer of ionic strength of about 8-50 millisiemens as measured by conductivity, for example about 100 to 500 mM phosphate buffer, at pH of about 5.5 to 7, and eluted using a buffer of increasing ionic strength or increasing pH, or both. Thus, active and inactive/latent forms of PAI-1 may be eluted separately from the cation exchange resin using a gradient of increasing ionic strength buffer at pH of about 5.5 to 7. A gradient of increasing pH (at constant buffer ionic strength) can alternatively be used to elute active and inactive/latent form PAI-1 into separate fractions from the cation exchange resin.

In view of this disclosure, it will be appreciated by persons skilled in the art of protein purification that a combination of increasing ionic strength and increasing pH can also be used to elute active and inactive form PAI-1. Thus, for example, at a higher buffer ionic strength, PAI-1 will elute from the cation exchange resin at a lower buffer pH than would be required to elute PAI-1 at a lower buffer ionic strength. Conversely, at a lower buffer pH, PAI-1 will elute at a higher buffer ionic strength than would be required to elute PAI-1 at a higher buffer pH.

We have also discovered a method for separating active form PAI-1, and inactive/latent form of PAI-1, comprising loading a sample containing both active and inactive/latent forms of PAI-1 to an anion exchange resin of 10-50 micron particle size and eluting active and inactive/latent forms of PAI-1 into separate fractions. The particle size of the cation exchange resin is preferably of relatively uniform particle size of 10-50 micron particle size. The sample loaded preferably contains at least 0.3 mg of total PAI-1 (both active and inactive/latent forms) per 1 mg of total protein.

The anion exchange resin may be loaded using a buffer of ionic strength of about 5-50 millisiemens as measured by conductivity and a pH of about 7.5-10. The buffer ionic strength of the sample loaded is preferably about 8-50 millisiemens.

Active and inactive/latent forms of PAI-1 are eluted into separate fractions from the anion exchange resin using a mobile phase buffer with a gradient of increasing ionic strength. Alternatively, active and inactive/latent forms of PAI-1 are eluted into separate fractions from the cation exchange resin using a mobile phase buffer with a gradient of decreasing pH. Active and inactive/latent forms of PAI-1 are also eluted into separate fractions from the cation exchange resin using a mobile phase buffer with a gradient of both increasing ionic strength and decreasing pH.

Active and inactive/latent forms of PAI-1 can be separated and purified by elution in separate fractions from an anion exchange resin, where the resin is loaded using a buffer of ionic strength of about 5-50 millisiemens as measured by conductivity, for example about 25 to 500 mM phosphate buffer, at pH of about 7.5 to 10, and eluted using either a buffer of increasing ionic strength or decreasing pH, or both.

It has also been discovered that optimum extraction and yield of soluble *E. coli*-expressed recombinant PAI-1 (rPAI-1) from the lysed host *E. coli* cells in a buffered solution is obtained when the ionic strength of the buffered solution is in the range of 8-25 millisiemens, and is preferably in the range of 15-22 millisiemens. The pH of the buffered solution used in the extraction process and may be in the range of about pH 5.5-10.

The unit of ionic strength used herein is a unit of conductivity, millisiemens The conductivity of a buffered solution is a function of the ionic strength. The term "millisiemens ionic strength" as used herein refers to the buffer solution ionic strength as measured by conductivity in a 1 cm path length cell at 24° C. in units of millisiemans. All conductivity values referred to herein are measured at 24° C. in a 1 cm path cell.

DETAILED DESCRIPTION OF THE INVENTION

Figure 1:
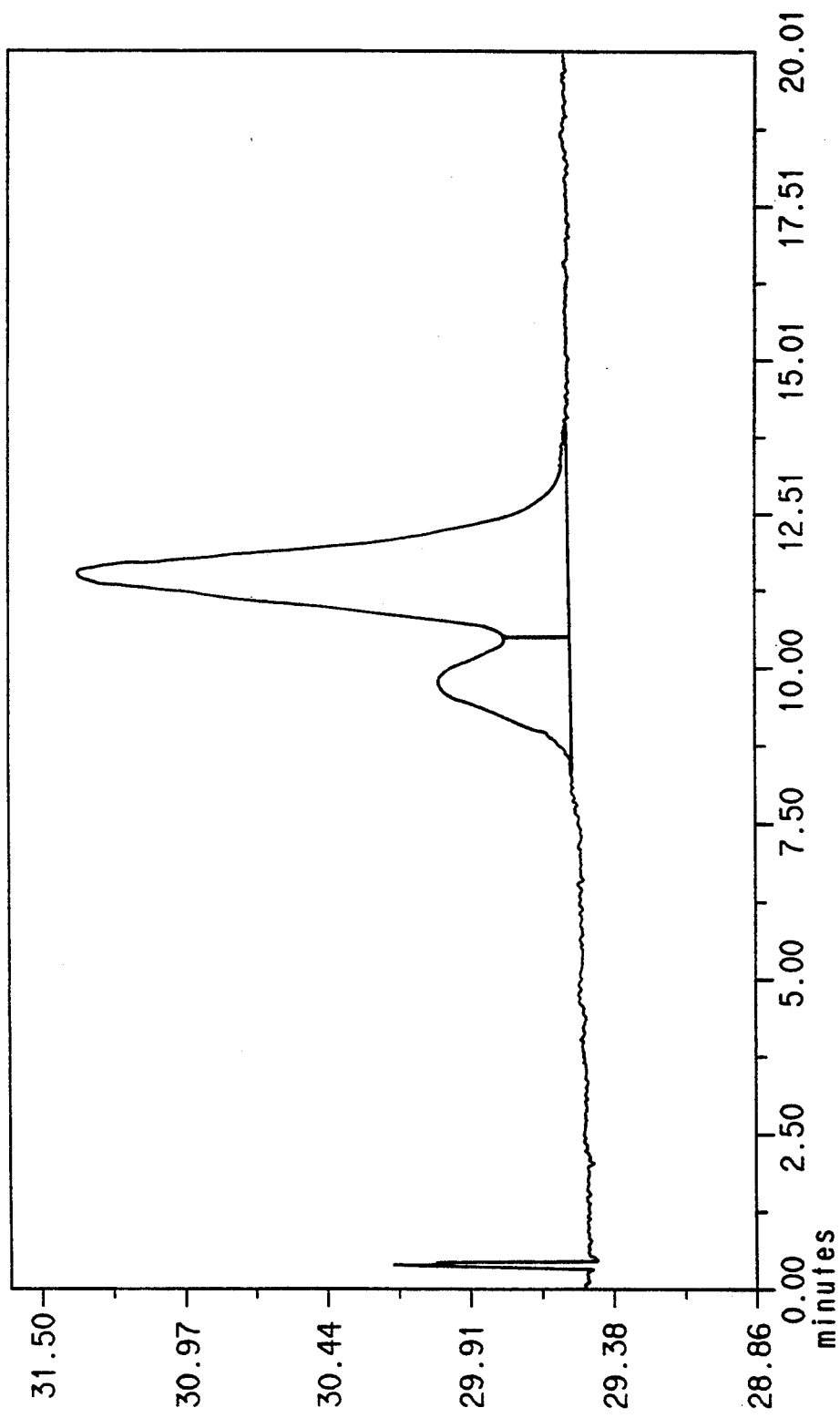
FIG. 1 shows a representative column chromatography elution profile of inactive/latent form PAI-1 (the first-eluting peak on the left) and active form PAI-1 (the second-eluting peak on the right) from a column containing Mono-Q Sepharose anion exchange resin (Pharmacia, Piscataway, N.J.). Elution of protein was monitored by absorption at 280 nm (y-axis) as a function of elution time (x-axis). Chromatography was carried out under conditions similar to those described in Example 2.

We have discovered a method for separating active form PAI-1, having a specific activity of greater than about 500,000 units/mg in the S-2251 assay, and inactive/latent form of PAI-1, having a specific activity of less than about 5,000 units/mg in the S-2251 assay, comprising loading a sample containing both active and inactive/latent forms of PAI-1 to a cation exchange resin of 10–50 micron particle size and eluting active and inactive/latent forms of PAI-1 into separate fractions. The particle size of the cation exchange resin is preferably of relatively uniform particle size of 10–50 micron particle size. By "relatively uniform particle size" it is meant that the particle sizes of the resin are in the range of about plus or minus 10–20%. The sample loaded preferably contains at least 0.3 mg of total PAI-1 (both active and inactive/latent forms) per 1 mg of total protein.

The cation exchange resin may be loaded using a buffer of ionic strength of about 5–50 millisiemens as measured by conductivity and a pH of about 5.5–7. The buffer ionic strength of the sample loaded is preferably about 8–50 millisiemens.

Active and inactive/latent forms of PAI-1 are eluted into separate fractions from the cation exchange resin using a mobile phase buffer with a gradient of increasing ionic strength. Alternatively, active and inactive/latent forms of PAI-1 are eluted into separate fractions from the cation exchange resin using a mobile phase buffer with a gradient of increasing pH. Active and inactive/latent forms of PAI-1 are also eluted into separate fractions from the cation exchange resin using a mobile phase buffer with a gradient of both increasing ionic strength and pH.

We have also discovered a method for separating active form PAI-1, and inactive/latent form of PAI-1, comprising loading a sample containing both active and inactive/latent forms of PAI-1 to an anion exchange resin of 10–50 micron particle size and eluting active and inactive/latent forms of PAI-1 into separate fractions. The particle size of the cation exchange resin is preferably of relatively uniform particle size of 10–50 micron particle size. The sample loaded preferably contains at least 0.3 mg of total PAI-1 (both active and inactive/latent forms) per 1 mg of total protein.

The anion exchange resin may be loaded using a buffer of ionic strength of about 5–50 millisiemens as measured by conductivity and a pH of about 7.5–10. The buffer ionic strength of the sample loaded is preferably about 8–50 millisiemens.

Active and inactive/latent forms of PAI-1 are eluted into separate fractions from the anion exchange resin using a mobile phase buffer with a gradient of increasing ionic strength. Alternatively, active and inactive/latent forms of PAI-1 are eluted into separate fractions from the cation exchange resin using a mobile phase buffer with a gradient of decreasing pH. Active and inactive/latent forms of PAI-1 are also eluted into separate fractions from the cation exchange resin using a mobile phase buffer with a gradient of both increasing ionic strength and decreasing pH.

We have discovered that active form and inactive/latent form PAI-1 can be resolved as distinct peaks of elution and distinct fractions of elution using either anion exchange chromatography or cation exchange chromatography, under the appropriate conditions. It was surprising that either anion or cation exchange chromatography would resolve active form and inactive/latent form PAI-1, since previous reports showed that these forms were not separable by sodium dodecyl sulfate polyacrylamide gel electrophoresis (SDS-PAGE), gel filtration, hydrophobic interaction chromatography (reverse phase), hydroxylapatite, heparin-agarose chromatography, or cation exchange chromatography (Lawrence et al., *Eur. J. Biochem.* (1989) 186:523–533). Previous reports have not disclosed the separation of active form and inactive/latent form PAI-1.

Previously we reported the purification of rPAI-1 using S-Sepharose (a mixture of 50–150 micron particle size) cation exchange chromatography, using 50 mM sodium phosphate buffer, pH 6.0 and eluting using 50 mM sodium phosphate buffer, pH 6.0 and a 0 to 1M NaCl gradient. The separation of active form and inactive/latent form PAI-1 was not evident using these conditions (Reilly et al.; *J. Biol. Chem.* (1990) 265:9570–9574).

We also reported previously the chromatography of rPAI-1 on Q-Sepharose (a mixture of 50–150 micron particle size) anion exchange resin, using 50 mM sodium phosphate pH 6.0. Under these condition rPAI-1, both active and inactive/latent forms, is not retained on the resin.

We have found that active and inactive/latent form PAI-1 can be separated and purified by elution in separate fractions from a cation exchange resin, where the resin is loaded using a buffer of ionic strength of about 8–50 millisiemens as measured by conductivity, for example about 100 to 500 mM phosphate, at pH of about 5.5 to 7, and eluted using a buffer of increasing ionic strength or increasing pH, or both. A buffer of increasing pH, up to about pH 7.5 to 10, may be used to elute PAI-1 from the cation exchange resin.

It has also been discovered that active and inactive/latent forms of PAI-1 can be separated and purified by elution in separate fractions from an anion exchange resin, where the resin is loaded using a buffer of ionic strength of about 5–50 millisiemens as measured by conductivity, for example about 25 to 500 mM phosphate buffer, at pH of about 7.5 to 10, and eluted using a buffer of either increasing ionic strength or decreasing pH, or both. A representative chromatogram of the separation of active and inactive/latent forms of PAI-1 by anion exchange chromatography is shown in FIG. 1.

Buffers useful in the present invention include standard buffers compatible with proteins and include, but are not limited to, ammonium carbonate, cacodylic acid, 4- or 5-hydroxymethyl-imidazole, pyrophosphoric acid, phosphoric acid, imidazole, 4- or 5-methylimidazole, triethanolamine, diethylbarbituric acid, 2,2-bis(hydroxymethyl)-2,2′,2″-nitrilotriethanol, $KH_2PO_4$, N-tris(hydroxymethyl)methyl-2-aminoethanesulfonic acid ("TES"), N-2-hydroxyethylpiperazine-N′-2-ethanesulfonic acid ("HEPES"), triethanolamine, tris(hydroxymethyl)-aminomethane ("Tris"), N-tris(hydroxymethyl)-methylglycine ("Tricine"), N,N-bis(2-hydroxyethyl)glycine ("Bicine"), borax, glycine, ammonia(acqueous)/$NH_4Cl$, ethanolamine, succinate/succinic acid, and 2-(N-morpholino)ethanesulfonic acid ("MES").

Salts useful in the present invention to increase buffered solution ionic strength include, but are not limited to, standard alkali metal salts commonly used in protein biochemistry.

Anion and cation exchangers suitable in the present invention are ion exchange hard beads of small and relatively uniform size, with particle size in the range of 10-50 microns. Cation exchange resins useful in the present invention include, but are not limited to, S-Sepharose HP (50 micron particle size) and Mono-S Sepharose (10 micron particle size) (Pharmacia, Piscataway, N.J.). Anion exchange resins useful in the present invention include, but are not limited to, Q-Sepharose HP (50 micron particale size) and Mono-Q Sepharose (10 micron particle size) (Pharmacia, Piscataway, N.J.). Suitable ion exchangers also include the following: DEAE-5-PW and SP-5-PW, produced by Tosoh and distributed by several suppliers including Waters and Bio-Rad Laboratories; CM-Si300 and DEAE-Si100, produced by Serva Feinbiochimica.

Two forms of PAI-1 are separated by ion exchange chromatography. The active form, designated as peak A or A form, has an activity of greater than about 500 units/μg in the S-2251 assay. The other form of PAI-1 is much less active, having an activity of less than 5 units/μg in the S-2251 assay. This inactive/latent form of PAI-1 is also designated as peak I or I form PAI-1.

The expression of rPAI-1 in *E. coli* is detailed in co-pending, commonly assigned U.S. patent application U.S. Ser. No. 07/350,264, filed May 11, 1989, the teaching of which is herein incorporated by reference. U.S. Ser. No. 07/350,264, also details procedures for the assay of the tPA inhibitory activity of PAI-1, including the S-2251 assay.

The S2251 assay measures the enzymatic ability of tissue plasminogen activator (t-PA) to generate plasmin from its plasminogen precursor by determining the level of amidolytic activity of generated plasmin on the chromogenic substrate D-Val-Leu-Lys-p-nitroanilide (S2251). The activity of PAI-1 in the S2251 assay is determined by measuring the inhibition by PAI-1 of the aforementioned plasmin amidolytic activity on the chromogenic substrate D-Val-Leu-Lys-p-nitroanilide. One unit of PAI-1 is defined as the amount of protein needed to neutralize 1 International Unit of t-PA in the S2251 assay (the activity of t-PA is expressed in IU by comparison with the International Reference Preparation for t-PA). Thus, by way of example, if it is determined that 25 ng of PAI-1 reduces the activity of 10 IU of t-PA by one-half, then the specific activity for the PAI-1 is taken as 5/25 or 0.2 units/ng.

Active form PAI-1 and inactive/latent form PAI-1, eluting under peak A and peak I during ion exchange chromatography, respectively, migrate identically during SDS-PAGE, elute at identical retention times in reverse phase high performance liquid chromatography (RPHPLC) on a C4 column using acetonitrile/water/TFA as mobile phase, and have the same N-terminal sequence. However, as stated above, PAI-1 under peak A differs from peak I in that peak A has an activity of greater than 500,000 units per mg in the S-2251 assay, while PAI-1 under peak I, when further purified to homogeneity, has an activity of less than 5000 units/mg.

Peak A and peak I PAI-1 can be separated using Pharmacia Mono-S chromatography (cation exchanger; 10 micron particle size) using the buffer system outlined above. Active and inactive form PAI-1 can also be separated by Pharmacia Mono-Q chromatography (anion exchanger; 10 micron particle size) using the buffer system outlined above. In the case of Mono-S chromatography, peak A elutes first and peak I second, whereas on the Mono-Q column the order of elution is reversed.

The ratio of peak A to peak I is found to vary somewhat from batch to batch and depends on how long the process has been carried out at a temperature greater than 10° C., i.e., the longer the material is kept at a temperature of 10° C. or greater, the more peak I relative to peak A. In order to stabilize active form PAI-1, the methods of the present invention are preferably carried out at a temperature of about 4°-10° C.

The column fractions are analyzed using SDS-PAGE and RPHPLC to determine purity and protein concentration, and ion exchange chromatography to determine the quantitative relative amount of active form and inactive/latent form PAI-1.

Column fractions containing PAI-1 may be pooled, filtered through a 0.22 μm filter, aliquoted, and stored at −70° C. The final product is checked by RPHPLC and SDS-PAGE for purity, by ion exchange chromatography to quantitate the relative amount of active form and latent/inactive form PAI-1, and by testing of tPA inhibitory activity. Typical preparations of PAI-1 have purity of greater than 95%, the percent peak A of greater than 80%, and the activity is greater than 500,000 units/mg in the S-2251 assay.

The Examples below present representative examples of the separation of active and inactive/latent forms of PAI-1 by cation and anion exchange chromatography. In the Examples below, active and inactive/latent forms of rPAI-1 are separated. Similar procedures are expected to be similarly useful for the separation of nonrecombinant PAI-1.

Figure 2:
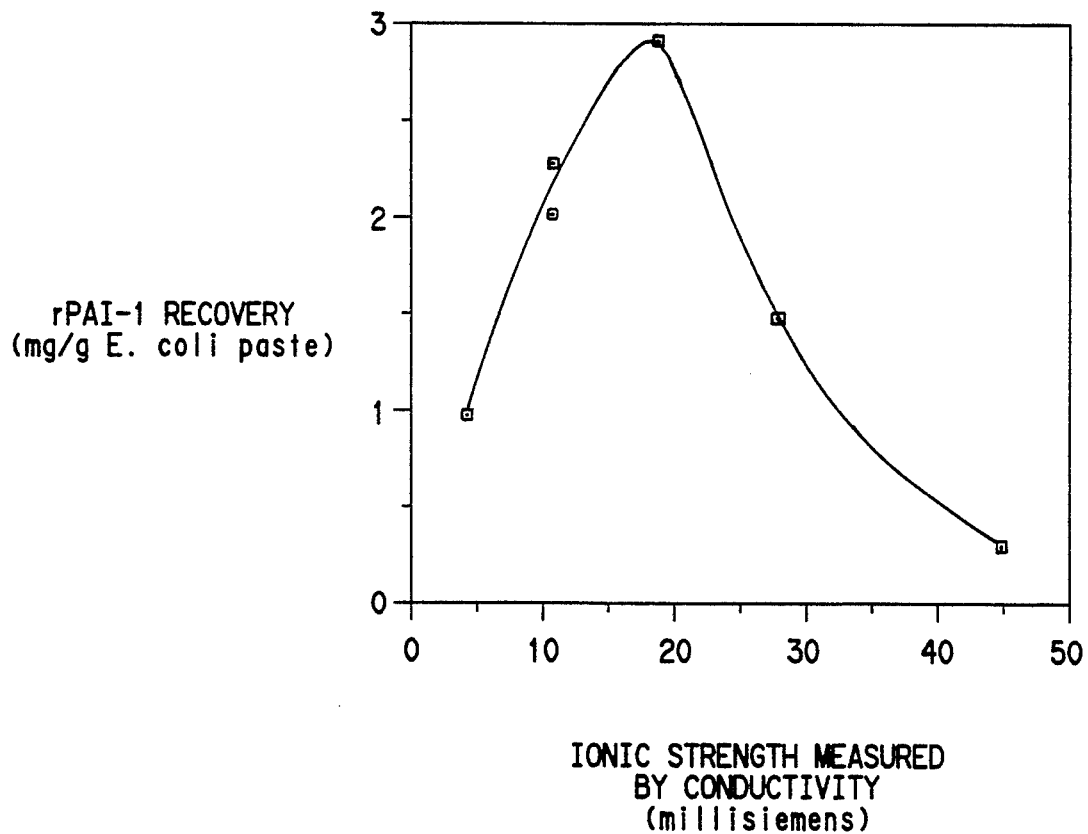
FIG. 2 shows the recovery of soluble rPAI-1 from an *E. coli* lysate as a function of solution ionic strength of the buffer in which the *E. coli* cells are lysed. The same data is presented in Table 1.

We have also discovered that optimum extraction and recovery of soluble *E. coli*-expressed recombinant PAI-1 (rPAI-1) from the lysed host *E. coli* cells in a buffered solution is obtained when the ionic strength of the buffered solution is in the range of 8-25 millisiemens, and is preferably in the range of 15-22 millisiemens. The pH of the buffered solution containing the lysed *E. coli* cells may be about 5.5-10. As shown in FIG. 2, the yield of soluble rPAI-1 from the *E. coli* lysate was markedly effected by the ionic strength of the buffered solution containing the lysed host *E. coli* cells.

In Example 3 below, the extraction of soluble *E. coli*-expressed rPAI-1 from an lysed host *E. coli* in a buffered solution is described for buffered solutions of varying ionic strength. In Example 3, the *E. coli* host is lysed by sonication. It is expected that a similar improved extraction of soluble rPAI-1 from an *E. coli* host will be obtained when the *E. coli* are lysed by other conventional methods such as homogenization, digestion with lysozyme, or pressure cycling.

EXAMPLE 1

Purification of Active Form PAI-1 by Cation Exchange Chromatography 3.305 kg of frozen *E. coli* cells containing PAI-1 protein were suspended in 13 kg of 150 mM sodium phosphate pH 6.0 by mixing with a 20 L Blakeslee mixer. Once the cells were thawed, the resulting slurry was poured through a 1000 mesh polypropylene screen into an additonal 20 kg of 150 mM sodium phosphate pH 6.0. The resulting slurry was maintained at 13° C. prior to the pass through the homogenizer. The homogenizer was set to a pressure of 8000 psi and the slurry was passed through at a rate of 850 mL/min. The cell homogenate, which was at 26° C., was then passed through a Sharples flow through centrifuge which had a centrifugal speed of 10,000 rpm. The Sharples was prechilled and the resulting semiclarified solution was chilled back down to 10° C. The Sharples removed 1.5 kg of cell debris.

The semi-clarified supernatant was pumped through three previously prepared QAE-3200 anion exchange cartridges (Cuno) at a flow rate of 540 mL/min. This step and all steps which follow took place in a cold room which operates at a temperature of 4° to 8° C. After the QAE step the flow-through containing the PAI-1 was then pumped through three previously prepared SP-800 cartridges (Cuno) (cation exchanger) at a flow rate of 200 mL/min. Once the entire QAE flow-through had been passed through the SP cartridges, the cartridges were washed with 20 L of 150 mM sodium phosphate pH 6.0 to wash all the cell debris out of the housing. The PAI-1 was then eluted using 150 mM sodium phosphate pH 8.6. The elution was collected in 1 L fractions, analyzed, and the pooled. The resulting PAI-1 pool was 80% pure by reverse phase high performance liquid chromatography (RPHPLC).

The Cuno ion exchange cartridges are not suitable for separation of active and latent/inactive forms of PAI-1; the single ion exchange sheet (rather than particles) does not provide the resolution necessary to separate the two forms of PAI-1.

An aliquot (about 1 L) containing about 1.2 gm of total protein was removed from the SP elution pool and the pH was adjusted to 6.0 with phosphoric acid or by dilution with 150 mM sodium phosphate pH 4.0. The resulting solution was loaded onto a 600 mL S-Sepharose HP (strong cation exchanger; 50 micron particle size) column (S-Sepharose HP by Pharmacia; column by Kronwald) at 64 cm of column height/hr. Following the sample load, additional 150 mM sodium phosphate pH 6.0 buffer was pumped onto the column until the detector, which monitored 220 nm, returned to the absorbance prior to the start of sample load. Then a linear gradient from 0 to 600 mM sodium chloride in 150 mM sodium phosphate, pH 6, was delivered to the column over a two hour time period.

During this elution the PAI-1 is resolved into two peaks. The first eluting form of PAI-1 has an activity of greater than about 500,000 units/mg in the S-2251 assay, and is designated peak A. The second peak containing PAI-1 has an activity of less than about 5,000 units/mg, and is designated peak I.

The ionic strength of peak A fractions was reduced by dilution 5-fold with 150 mM phosphate, pH 6.0 using 2 pumps during loading onto a sequential set of two previously prepared DEAE-250 anion exchange capsules (Cuno) and two SP-250 cation exchange capsules (Cuno). Once the samples are loaded onto the sequential set, the DEAE capsules are removed and the resulting SP capsules are washed with 3 liter of 150 mM sodium phosphate pH 6.0. The bound peak A PAI-1 is then eluted with 150 mM sodium phosphate, pH 8.6. The elution is collected as 100 mL aliquots which are analyzed by RPHPLC, SDS-PAGE, and tPA inhibitory activity to determine appropriate pooling. The peak A PAI-1 pool is then filtered through a 0.22 μm filter, aliquoted, and stored frozen at −70° C.

The purpose of the final Cuno ion exchange capsule step is to remove endotoxin and to concentrate the PAI-1.

EXAMPLE 2

Separation of Active and Inactive/latent Forms of PAI-1 by Anion Exchange Chromatography Cell Lysate Preparation: 1.5 g +/−0.02 g of cell paste was weighed out into a 30 mL centrifuge tube. 15 grams of Buffer-1 (150 mM sodium phosphate monobasic, pH 6.0) was added. The sample was then shaken until the paste was completely resuspended (10–20 min at 4° C.). The cell suspension was then sonicated on ice using an intermediate tip positioned 1 cm from the platform and off-center in the tube (4×1 minute; 100% duty, power 4.0). The sample was allowed to cool to about 1°–4° C. between sonications. The sonicated samples were then centrifuged in the same tube at 13,000 rpm for 30 minutes in a Du Pont RC5B centrifuge with rotor pre-chilled to 4° C.

Preparation of Cartridges: Cuno QAE-60 anion exchange cartridges were pumped with 50 mL of 50 mM phosphate, 1.0M sodium chloride at 5 mL/min. The Cuno SP-60 cation exhcange cartridges are ready as provided by the supplier. Isolation of PAI-1: One QAE-60 cartridge and one SP-60 cartridge were coupled in series with the QAE first. 150 mL of Buffer-1 was then pumped through the coupled set using a flow rate of 5 mL/min. The sample was then loaded onto the cartridges at 0.5 mL/min. When the sample was finished loading, another 15 mL of Buffer-1 was pumped onto the cartridges at 0.5 mL/min. The QAE cartridge was then removed and another 25 mL of Buffer-1 was then pumped through the SP cartridge at 2 mL/min. Most of the liquid from SP cartride was removed by gently pushing air through the cartridge. Once the liquid was no longer flowing, 20 mL of Buffer-2 (150 mM sodium dibasic phosphate, pH adjusted to 8.6 with phosphoric acid) was pumped onto the cartridge at 2 mL/min. After all the liquid was pumped through the SP cartridge, most of the liquid was removed from the cartridge using forced air. All of the 20 mL of Buffer-2 elution was collected in a single fraction. Samples were immediately frozen and held at −70° C. until ready to be chromatographed further. This entire is process performed at 4°–8° C.

Anion Exchange Determination of the Relative Amount of Active and Inactive/latent Forms of PAI-1: Samples, as prepared above, were thawed and diluted with 4 volumes of Buffer-3 (50 mM ammonium carbonate, pH 9.0). The diluted samples were injected (100 μL) into a Hewlett Packard 1090 HPLC equipped with an analytical Pharmacia Mono-Q (anion exchange resin; 10 micron particle size) FPLC column. The column flow rate was maintained at 2 mL/min and immediately following injection of the sample a linear gradient was begun with Buffer-3 containing 1.0M NaCl. The gradient slope was such that in 20 minutes the elution solvent was 30% of the Buffer-3 containing 1.0M NaCl. Protein elution was monitored by adsorption at 280 mm.

Inactive/latent form PAI-1 eluted from the column first at approximately 9.3 min, and active form PAI-1 eluted at approximately 10.9 min. Integration of the relative areas under the two peaks and comparison with standard samples allows quantitation of the relative amount of active and inactive/latent forms of PAI-1.

EXAMPLE 3

Extraction of Soluble *E. coli*-expressed Recombinant PAI-1 From *E. coli*

The effect of buffer ionic strength of the buffer in which *E. coli* expressing recombinant PAI-1 (rPAI-1) are lysed on the extraction and recovery of soluble rPAI-1 from *E. coli* was examined. A cell lysate was prepared from *E. coli* containing rPAI-1 according to the procedure under Example 2 except that the composition of Buffer-1 was varied in ionic strength by increasing either the sodium phosphate monobasic concentration or adding NaCl to the buffer, as shown in Table 1 and FIG. 2. Following cell lysate preparation, PAI-1 was purified by chromatography using Cuno QAE-60 and SP-60 cartridges in series, as described under Example 2.

Following Cuno QAE-60 and SP-60 cartridge chromatography, total rPAI-1 was quantitated by reverse phase HPLC on a C4 column using acetonitrile/water/TFA as mobile phase (RPHPLC). Active and inactive/latent forms of PAI-1 are not separated by RPHPLC. The amount of total rPAI-1 was quantitated by peak area relative to known amounts of rPAI-1 run as a standard. The recovery of soluble rPAI-1 following extraction from *E. coli* using buffered solutions of varying ionic strength is shown in Table 1 and FIG. 2.

TABLE 1

| Buffer | Conductivity (millisiemens) | rPAI-1 Recovery (mg/g *E. coli* paste) |
| --- | --- | --- |
| 50 mM phosphate, pH 8.6 | 4.21 | 0.97 |
| 50 mM phosphate, pH 8.6, 1 M NaCl | 10.8 | 2.29 |
| 150 mM phosphate, pH 8.6 | 10.8 | 2.02 |
| 300 mM phosphate, pH 8.6 | 18.8 | 2.91 |
| 500 mM phosphate, pH 8.6 | 27.9 | 1.48 |
| 1 M phosphate, pH 8.6 | 44.8 | 0.30 |

As shown in Table 1 and FIG. 2, the recovery of rPAI-1 from an *E. coli* lysate is increased substantially when the buffer ionic strength of the lysate is in the range of 8–25 millisiemens, and preferably in the range of 15–22 millisiemens.

What is claimed is:

1. A method for separating active form PAI-1, having a specific activity of greater than about 500,000 units/mg in the S-2251 assay, and inactive/latent form PAI-1, having a specific activity of less than about 5000 units/mg in the S-2251 assay, comprising:
   (a) loading a sample containing a mixture of active and inactive/latent forms of PAI-1 to a carton exchange resin of 10–50 micron particle size; and
   (b) eluting active and inactive/latent forms of PAI-1 into separate fractions using a mobile phase buffer with a gradient, wherein the gradient is selected from:
   a gradient of increasing ionic strength,
   a gradient of increasing pH, or
   a gradient of increasing ionic strength and increasing pH,
   under conditions where active and inactive/latent forms of PAI-1 are eluted from the resin in separate fractions.

2. A method of claim 1 wherein the sample loaded to the cation exchange resin contains at least 0.3 mg of active and inactive/latent forms of PAI-1 per mg of total protein.

3. A method of claim 1 wherein the sample loaded is a buffered solution of pH 5.5–7.

4. A method of claim 2 wherein the sample loaded is a buffered solution of pH 5.5–7.

5. A method of claim 1 wherein the sample loaded is a buffered solution of 8–50 millisiemens ionic strength.

6. A method of claim 2 wherein the sample loaded is a buffered solution of 8–50 millisiemens ionic strength.

7. A method of claim 3 wherein the sample loaded is a buffered solution of 8–50 millisiemens ionic strength.

8. A method of claim 4 wherein the sample loaded is a buffered solution of 8–50 millisiemens ionic strength.

9. A method of claim 1 wherein the cation exchange resin particles are of relatively uniform particle size.

10. A method of claim 1 wherein the sample loaded is a buffered solution of 5–50 millisiemens ionic strength.

* * * * *